US00PP25719P3

(12) United States Plant Patent

Jones et al.

(10) Patent No.: US PP25,719 P3

(45) Date of Patent: Jul. 14, 2015

(54) *DIASCIA* PLANT NAMED 'AURORA DARK PINK'

(50) Latin Name: *Diascia×hybrida*
Varietal Denomination: Aurora Dark Pink

(71) Applicants: Sidney James Jones, Gwent (GB); David James Jones, Caldicot (GB)

(72) Inventors: Sidney James Jones, Gwent (GB); David James Jones, Caldicot (GB)

( * ) Notice: Subject to any disclaimer, the term of this patent is extended or adjusted under 35 U.S.C. 154(b) by 154 days.

(21) Appl. No.: 13/986,681

(22) Filed: May 23, 2013

(65) Prior Publication Data

US 2014/0352019 P1 Nov. 27, 2014

(51) Int. Cl.
*A01H 5/00* (2006.01)

(52) U.S. Cl.
USPC ..... Plt./425

(58) Field of Classification Search
USPC ..... Plt./425
See application file for complete search history.

(56) References Cited

PUBLICATIONS http://www.newplantsandflowers.com/diascias-with-outstanding-retail-appeal/. Mar. 19, 2013.*

* cited by examiner

*Primary Examiner* — Annette Para
(74) *Attorney, Agent, or Firm* — Barbara Campbell; Cochran Freund & Young LLC

(57) ABSTRACT

A new cultivar of *Diascia* plant named 'Aurora Dark Pink' that is characterized by compact plant habit and elongated racemose inflorescences consisting of many dark pink flowers with red eyes, is disclosed.

2 Drawing Sheets

Genus and species: *Diascia×hybrida*.
Variety denomination: 'Aurora Dark Pink'.

BACKGROUND OF THE NEW PLANT

The present invention relates to a new and distinct cultivar of twinspur, which is grown as a spring and summer flowering annual or perennial plant for use in containers, borders and in mass landscape planting. The new cultivar in the genus *Diascia* will be referred to hereinafter by the cultivar name 'Aurora Dark Pink'. This application is co-pending with the related cultivars *Diascia* 'Aurora Light Pink' and *Diascia* 'Aurora Apricot' which have been hybridized and selected in the same manner.

The inventors have been interested and have collected plants of the genus *Diascia* since the early 1990s. *Diascia*, which is native to southern Africa, provides showy annual and perennial (in mild climates) plants whose predominant flower color range in nature is in the range of soft to dark pink, also white, lavender-pink, salmon and apricot. Plants of *Diascia* which are raised from seed are inherently variable in growth habit; ranging from loose, weak plants with brittle stems to plants with significantly shorter internodes. Various breeding programs, including the inventors', have aimed to develop improvements in plant habit and also an extension of the color range into the deep pink, red or orange shades and ideally with very similar compact habits for each color.

Commencing in or around 1998, the inventors commenced a breeding project to develop a uniform series of *Diascia* which exhibit flowers held erect and above the foliage, in a range of colors, and borne on plants with compact habit. By 2003, the inventors had isolated certain seedlings which presented stiffly-held longer racemes of individual flowers. Although the inventors deliberately selected and set aside parents for their presumed usefulness for immediate and future hybridization, the parents themselves were not released but given code names for the inventors' use. The female parent is known under code '9D423' and the male parent is known under code '9D3102'. The inventors estimate that approximately thirty generations of crosses preceded the selection of 'Aurora Dark Pink' in 2009. 'Aurora Dark Pink' was selected by the inventors as an individual seedling within a population of many hundreds of seedlings which flowered in that year. 'Aurora Dark Pink' was selected by the inventors for its combination of qualities including length of inflorescence, arrangement of individual flowers within the inflorescence, clarity of flower color, compatibility and uniformity with other candidates for a related series.

The first asexual propagation of 'Aurora Dark Pink' was conducted in 2009 by the inventors at their nursery in Newport, Gwent, England. The method of asexual propagation used was vegetative tip cuttings. Since that time the unique and distinguishing characteristics of 'Aurora Dark Pink' has been determined stable, fixed, and reproduces true to type in successive generations of asexual reproduction.

SUMMARY

The following traits have been repeatedly observed and represent the characteristics of the new *Diascia* cultivar 'Aurora Dark Pink'. 'Aurora Dark Pink' has not been tested under all possible conditions and phenotypic differences may be observed with variations in environmental, climatic, and cultural conditions, without however, any difference in genotype.

1. 'Aurora Dark Pink' exhibits compact habit.
2. The inflorescence of 'Aurora Dark Pink' consists of individual flowers which are arranged in an elongated raceme.
3. The quantity of flowers which are borne in a single inflorescence during its life ranges between 25 and 35, of which 15 to 20 are fully open at any one time.
4. 'Aurora Dark Pink' exhibits spires of dark pink flowers.
5. Each flower of 'Aurora Dark Pink' exhibits a red eye.
6. 'Aurora Dark Pink' blooms profusely spring through fall.
7. 'Aurora Dark Pink' exhibits glossy mid green colored foliage.
8. 'Aurora Dark Pink' is propagated using the method of vegetative tip cuttings.
9. 'Aurora Dark Pink' is fast growing. A spring planted young plant fills and flowers in a 10.0 cm container in six to eight weeks from spring transplanting.
10. The cultural requirements of 'Aurora Dark Pink' are well-draining soil, full sun, and regular water.
11. 'Aurora Dark Pink' is suitable for use in raised beds, borders, hanging baskets, and patio containers.
12. 'Aurora Dark Pink' is hardy to USDA Zone 8.

COMPARISON WITH KNOWN VARIETY AND PARENTAL LINES

Whereas the flower color of 'Aurora Dark Pink' is dark pink in color with a red eye, the flowers of the comparison plant 'Aurora Apricot' (U.S. Plant patent application Ser. No. 13/986,666) are apricot with a dark orange eye.

When 'Aurora Dark Pink' is compared to the female seedling parent '9D423', the flower eye of 'Aurora Dark Pink' is lighter in color than the female parent. When 'Aurora Dark Pink' is compared to the male seedling parent '9D3102', the foliage growth of 'Aurora Dark Pink' is more compact than '9D3102'.

DESCRIPTION OF THE PHOTOGRAPHS

The accompanying color photographs FIG. 1 and FIG. 2 illustrate the overall appearance of the new *Diascia* cultivar 'Aurora Dark Pink' showing the colors as true as it is reasonably possible to obtain in colored reproductions of this type. Colors in the photographs may differ from the color values cited in the detailed botanical description, which accurately describes the actual colors of the new variety of *Diascia* named 'Aurora Dark Pink'. Both photographs have been made using conventional photographic techniques and although colors may appear different from actual colors due to light reflectance, they are as accurate as possible by conventional photography.

DESCRIPTION OF THE NEW VARIETY

Figure 1:
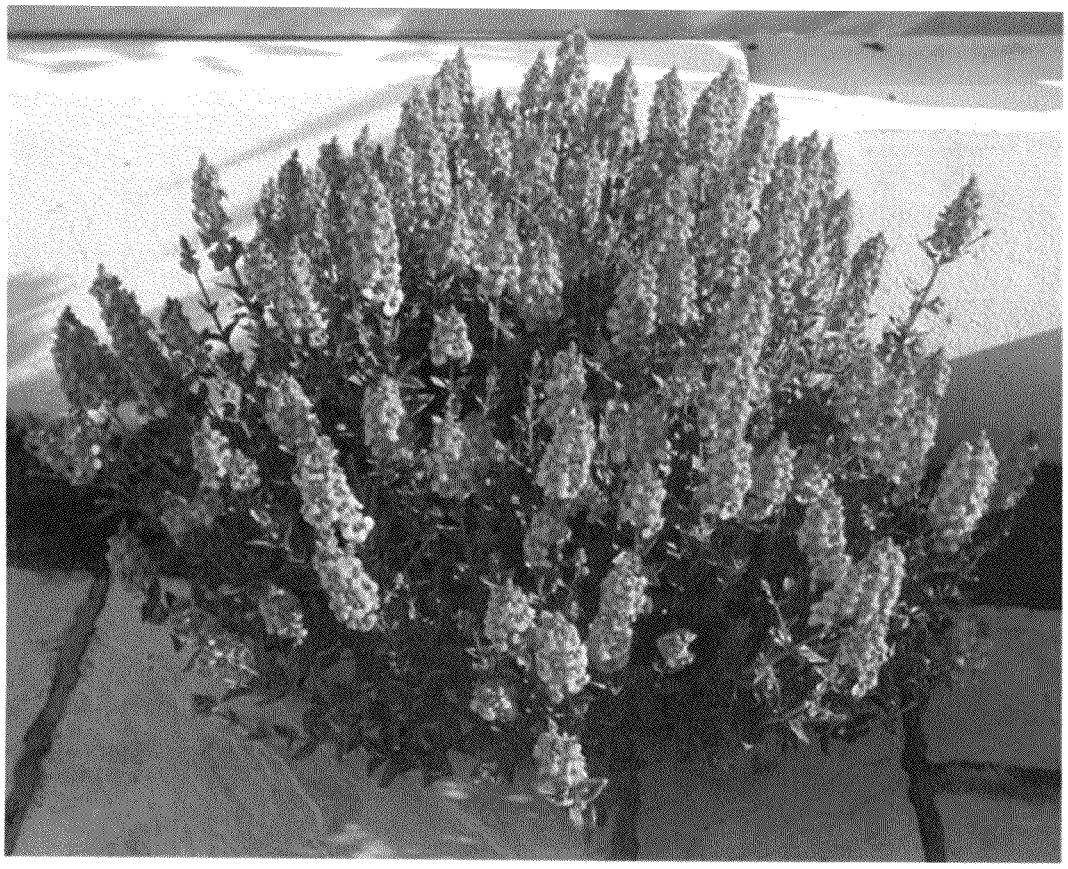
FIG. 1 depicts one whole plant of 'Aurora Dark Pink' which is growing and flowering in mid-summer out of doors in Newport, Gwent, England. The illustrated plant was started from a rooted cutting approximately 10 months previously and maintained in a frost-free greenhouse until placing outdoors in spring.
Figure 2:
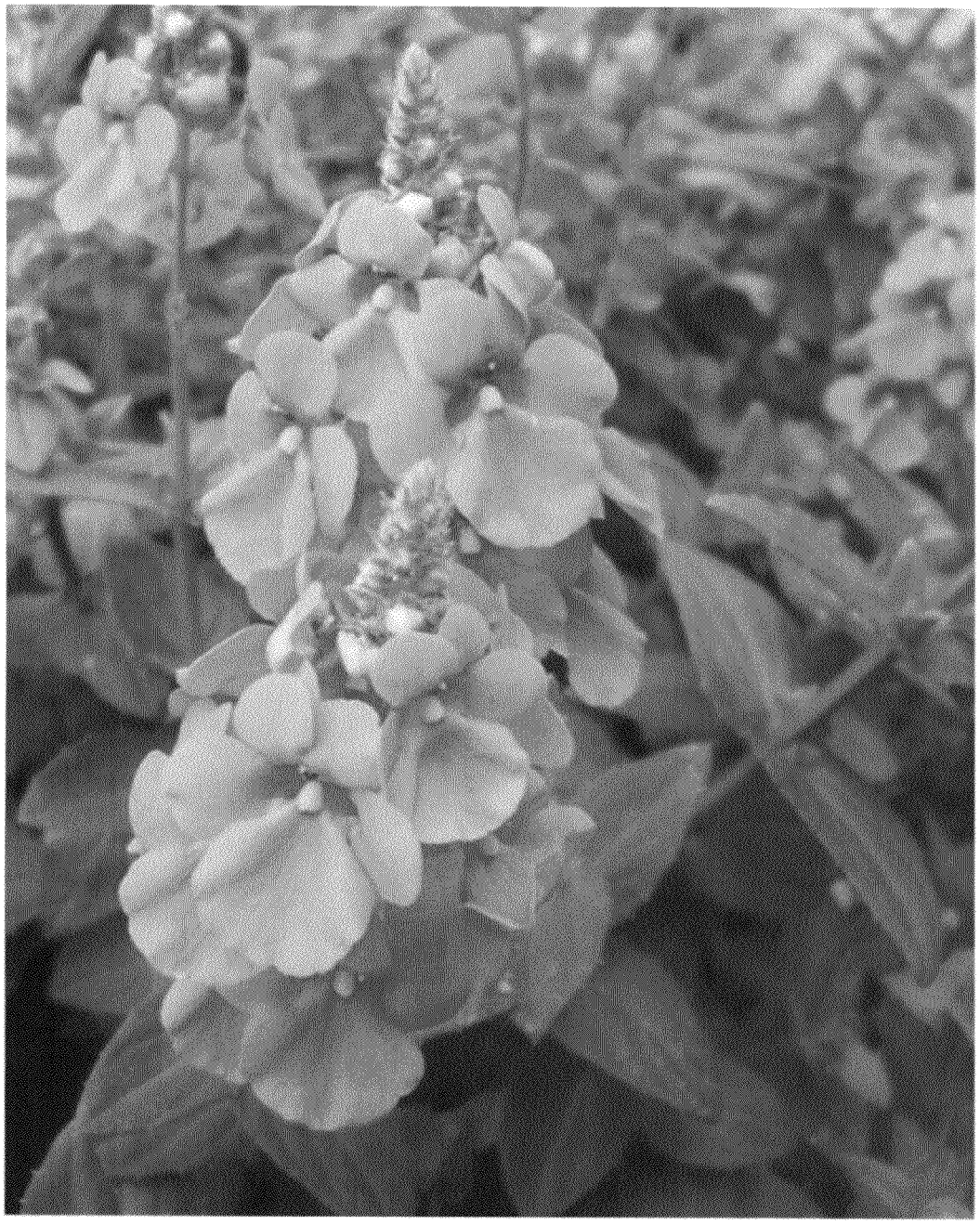
FIG. 2 illustrates the racemose inflorescence of 'Aurora Dark Pink' together with the individual dark pink flowers and red eyes.

The following is a detailed description of the new *Diascia* cultivar 'Aurora Dark Pink'. Data was collected April 2013 in Santa Barbara, Calif. from five-month-old plants planted in the garden border. The color determinations are in accordance with the 2007 edition of The Royal Horticultural Society Colour Chart, except where general color terms of ordinary dictionary significance are used. The new *Diascia* variety named 'Aurora Dark Pink' has not been observed under all possible environmental conditions. Phenotypic differences may be observed with variations in environmental, climatic, and cultural conditions, without however, any difference in genotype.

Classification:

*Botanical classification.*—*Diascia×hybrida.*

*Denomination.*—'Aurora Dark Pink'.

*Common name.*—Twinspur.

*Commercial classification.*—Annual or perennial.

Parentage: The female parent is known under code '9D423' and the male parent is known under code '9D3102'. Both parents are unreleased and unpatented.

Plant:

*Plant uses.*—Suitable for use in containers, borders and mass landscape plantings.

*Cultural requirements.*—Provide well-draining soil, full sun and regular water; trimming when young will encourage strong basal branching.

*Hardiness.*—Hardy to USDA Zone 8.

*Blooming seasons.*—Spring, summer and fall.

*Plant habit.*—Compact.

*Plant form.*—Mounding.

*Plant vigor.*—Vigorous.

*Plant propagation method.*—Propagated using the method of vegetative tip cuttings.

*Production time.*—Six to eight weeks are required to produce a flowering plant in a quart or 10.0 cm diameter container; ten to twelve weeks are required to produce a full flowering plant in a 1 gallon or 15.0 cm diameter container.

*Plant height (foliage mound).*—12.0 cm to 15.0 cm.

*Plant height (including flowers).*—30.0 cm to 35.0 cm.

*Plant width.*—25.0 cm to 30.0 cm.

*Root system.*—Fine and fibrous roots.

*Resistance and susceptibility to diseases and pests.*—No resistance or susceptibility to pests or disease is known to the inventor.

*Time to develop roots.*—10 to 14 days are needed to develop roots on an initial cutting.

*Special considerations.*—Encourage new branching by periodic pruning.

Stems:

*General.*—Stem produces 3 to 4 branching stems at 1.0 cm above surface; each branching stem produces 1 to 2 nodal sub-branches.

*Flowering stems per plant.*—Approximately 100 during the year.

*Stem shape.*—Quadrilateral.

*Stem color.*—RHS 138B.

*Stem dimensions.*—15.0 cm in length, 4.0 mm in diameter.

*Internode length.*—Ranges from 2.0 cm to 4.50 cm.

*Stem surface.*—Smooth, glabrous.

Leaves:

*Number of leaves per branching stem.*—8 to 10.

*Leaf arrangement.*—Opposite.

*Leaf division.*—Simple.

*Leaf shape.*—Cordate.

*Leaf base.*—Cordate.

*Leaf apex*.—Acute.
*Leaf margin*.—Denticulate, teeth spaced at 5.0 mm, depth 1.0 mm.
*Leaf venation pattern*.—Pinnate.
*Vein color* (*adaxial surfaces*).—RHS 138A.
*Vein color* (*abaxial surfaces*).—RHS 138A.
*Leaf surface* (*both surfaces*).—Glabrous.
*Leaf color* (*adaxial surface*).—RHS 138A.
*Leaf color* (*abaxial surface*).—RHS 137B.
*Leaf dimensions*.—3.5 cm in length, 2.0 cm in width.
*Leaf attachment*.—Sessile.

Inflorescence and flowers:
*Inflorescence type*.—Terminal raceme.
*Quantity of inflorescences per plant*.—5 to 8 on a five-month old plant.
*Inflorescence dimensions*.—15.0 cm in length; 4.5 cm in diameter.
*Quantity of flowers developed during inflorescence life*.—25 to 35.
*Quantity of fully open flowers at any time per inflorescence*.—15 to 20.
*Rate of flower opening*.—3 to 4 days from first color to fully open flower.
*Blooming months*.—Flowers bloom April through November.
*Lastingness of flower*.—An individual flower lasts from 4 to 6 days on the plant.
*Flower fragrance*.—None.
*Flower description*.—Type is solitary.
*Flower aspect*.—Outward-facing.
*Flowers persistent or self-cleaning*.—Self-cleaning.
*Flower shape*.—Personate with twin calcars (spurs).
*Flower dimensions*.—1.8 cm in height, 1.5 cm in width, 1.0 cm in depth.
*Flower color*.—RHS 47C with RHS 45B eye.
*Petals*.—5, basally fused.
*Petal surface*.—Glabrous.
*Petal margin*.—Entire.
*Petal apex*.—Obtuse.
*Petal base*.—Rounded.
*Petal shape*.—Orbicular.
*Petal dimensions* (*uppermost pair*).—8.0 mm in height, 6.0 mm in width.
*Petal dimensions* (*lateral pair*).—15.0 mm in height, 12.0 mm in width.
*Petal dimensions* (*lowest*).—18.0 mm in height, 18.0 mm in width.
*Petal color* (*both surfaces*).—RHS 47C becoming RHS 45B at the base.
*Corolla window color*.—RHS 155C.
*Corolla window dimensions*.—2.0 mm in length and 2.0 mm in width.
*Pollinator guide spot*.—Located at base (where fused) of uppermost petals; diameter 3.0 mm, color RHS 10A.
*Calcar*.—2 in number.
*Calcar surface*.—Glabrous.
*Calcar dimensions*.—6.0 mm in depth and 2.0 mm in diameter.
*Calcar color*.—RHS 31B.
*Bud shape*.—Globose.
*Bud surface*.—Stipitate-glandular.
*Bud color* (*immediately prior to cracking color*).—RHS 146A.
*Bud dimensions*.—4.0 mm in length and 4.0 mm in width.
*Peduncle color*.—RHS 146B becoming RHS 173B above uppermost leaf node.
*Peduncle dimensions*.—5.0 cm to 8.0 cm in length, 1.5 mm in diameter.
*Peduncle shape*.—Quadrilateral.
*Peduncle surface*.—Stipitate-glandular.
*Pedicel color*.—RHS 173B.
*Pedicel dimensions*.—0.8 cm in length, 0.5 mm in width.
*Pedicel shape*.—Cylindrical.
*Pedicel surface*.—Stipitate-glandular.
*Calyx shape*.—Stellate.
*Calyx color*.—RHS 146B.
*Number of sepals*.—5, unfused.
*Sepal color* (*adaxial and abaxial surfaces*).—RHS 146B.
*Sepal surface*.—Stipitate-glandular.
*Sepal shape*.—Oblanceolate.
*Sepal dimensions*.—4.0 mm in length and 0.75 mm in width.
*Sepal apex*.—Acute.
*Sepal base*.—Truncate.
*Sepal margin*.—Entire.

Reproductive organs:
*Stamens*.—4.
*Stamen color*.—RHS N186C.
*Stamen dimensions*.—4.0 mm in length and 0.50 mm in width.
*Anthers*.—Tiny, ellipsoid, less than 1.0 mm in length, width; color RHS 7C.
*Quantity of pollen*.—Slight.
*Color of pollen*.—RHS 7C.
*Pistil* (*style and stigma*).—Tiny protrusion, mid brown, less than 1.0 mm in height.
*Ovary*.—Superior, globose, 1.0 mm to 2.0 mm in diameter, color close to RHS 151C.
*Seed*.—Found occasionally, round, diameter 1.0 mm, color mid brown.

We claim:

1. A new and distinct variety of *Diascia* plant designated 'Aurora Dark Pink' as illustrated and described herein.

* * * * *